US006255278B1

(12) United States Patent
Pierpaoli

(10) Patent No.: US 6,255,278 B1
(45) Date of Patent: *Jul. 3, 2001

(54) COMPOSITION CONTAINING POOLED TRANSFERRINS AS AN ACTIVE PRINCIPLE FOR THE INDUCTION OF IMMUNE TOLERANCE AGAINST ANTIGENS

(75) Inventor: Walter Pierpaoli, Bellinzona (CH)

(73) Assignees: Cellena AG, Ebmatingen (CH); I.S.I. S.p.A., Pascoli (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/836,389

(22) PCT Filed: Nov. 3, 1995

(86) PCT No.: PCT/EP95/04317

§ 371 Date: Aug. 12, 1997

§ 102(e) Date: Aug. 12, 1997

(87) PCT Pub. No.: WO96/14862

PCT Pub. Date: May 23, 1996

(30) Foreign Application Priority Data

Nov. 10, 1994 (EP) .................................................. 94402554

(51) Int. Cl.[7] .......................... A61K 38/00; A61K 38/24; A61K 38/40; A61K 39/00
(52) U.S. Cl. .................................. 514/2; 514/6; 514/21; 530/399; 530/400; 424/93.73; 424/184.1; 424/198.1; 424/278.1; 424/529; 424/530; 424/534

(58) Field of Search ................... 514/2, 6, 21; 530/399, 530/400; 424/93.73, 184.1, 198.1, 278.1, 529, 530, 534

(56) References Cited

FOREIGN PATENT DOCUMENTS

0426921 * 5/1991 (EP) .

OTHER PUBLICATIONS

Pierpaoli Et Al., *Cellular Immunology*, vol. 134, pp. 225–234, 1991.*

*Medical Immunology*, Edited by James Irvine, Teviot Scientific Publication, Great Britain, 1979.*

Pierpaoli Et Al, *Biological Abstracts*, vol. 95, Abstract No. 54425, 1993 (Nat. Immun. vol. 11, No. 6, pp. 356–365, 1992).*

* cited by examiner

*Primary Examiner*—Avis M. Davenport
*Assistant Examiner*—Abdel A. Mohamed
(74) *Attorney, Agent, or Firm*—Leonard R. Svensson; Birch, Stewart, Kolasch & Birch, LLP

(57) ABSTRACT

A method for controlling immune reactions to a foreign tissue or a foreign cell in a recipient host mammal to enhance tolerance of the recipient host mammal towards a grafted foreign tissue or a grafted foreign cell. This method involves administering a transferrin and a foreign tissue or a foreign cell antigen from the same genetic donor to a previously immunosuppressed recipient host mammal.

18 Claims, 2 Drawing Sheets

COMPOSITION CONTAINING POOLED TRANSFERRINS AS AN ACTIVE PRINCIPLE FOR THE INDUCTION OF IMMUNE TOLERANCE AGAINST ANTIGENS

BACKGROUND OF THE INVENTION

1. Field of the Invention

The invention relates to the production of compositions, particularly pharmaceutical compositions, containing an active principle capable of controlling the immune reactions of a host against allogeneic cells or tissues or of immunocompetent cells against an immunoincompetent or immunosuppressed host, particularly those immune reactions which are involved in the so-called host versus-graft reaction (HvGR) and so-called graft versus-host reaction (GvHR) or graft versus-host disease (GvHD), as well as immune reactions which are brought into play in bone marrow transplantation (BMT), i.e. when the host is transplanted with allogeneic or xenogeneic incompatible bone marrow.

2. Description of the Prior Art

Series of studies have been initiated in 1978 by the inventor relative to the bone-marrow-engraftment-promoting activity of bone-marrow-derived factors (Pierpaoli W. et al, Transplantation 1978; 26:456–458) and (Pierpaoli W. et al, J. Clin. and Lab. Immunol. 1985; 16:115–124). The initial observation was that the supernatant of a solution in which the bone marrow cells had been suspended (bone marrow supernatant: BM-SN) provided an engraftment-enhancing activity (Pierpaoli W. et al, Cell Immunol 1980; 52:62–72). This indicated the presence of factors able to modify the capacity of the bone marrow to be engrafted in an irradiated host for induction of permanent allogeneic or xenogeneic chimerism.

An extensive series of experiments further demonstrated that high-molecular-weight fractions obtained by ultrafiltration through porous membranes of the native BM-SN derived from rabbit marrow contained marrow-regulating factors (MRF) capable of exerting the same effect, i.e. of inducing hemopoietic chimerism across the H-2 barrier in the murine model (Pierpaoli W. et al, Cell Immunol 1981; 57:219–228). However, the results obtained are not easily reproduced, at least quantitatively; there is considerable variability in the results and the incidence of secondary disease is high. Moreover, induction of chimerism was not achieved in all of the murine H-2 combinations tested (Pierpaoli W. et al, J Lab Clin Immunol 1985;16:115–124).

More recently separation-and characterization of a specific component from rabbit bone-marrow-derived fractions, namely transferrin, has been reported. It is now considered to be responsible for the facilitation of allogeneic and xenogeneic bone marrow engraftment that had been achieved earlier with rabbit and bovine, marrow-derived fractions (European Patent application No. EP89403103.8/ 0426924 Pierpaoli W. et al, Cell Immunol 1981;57:219–228 and Pierpaoli W. et al, J Lab Clin Immunol 1985;16:115–124). Treating lethally irradiated C57BL/6 mice transplanted with bone marrow from BALB/c donors with iron-saturated human transferrin and conalbumin, resulted in remarkably stable engraftment, avoidance of GvHD and enduring chimerism in the majority of test animals (Pierpaoli W. et al, Cell Immunol 1991;134:225–234). But again, additional work seeking to evaluate the engraftment-promoting activity of human transferrin in other H2-incompatible murine combinations were not in all instances as successful.

No effect of human transferrin was observed in C57BL/6 mice grafted with marrow from C3H/He donors and in which marrow from C57BL/6 mice was transplanted into C3H/He mice. Accordingly, it seemed that the promoting effects of transferrin was rather varying according to the histogenetic H-2-type combination used, the promoting effect being maximal in C57BL/6 mice (H-$2^b$) grafted with BALB/c (H-$2^d$) marrow and absent in C57BL/6 mice grafted with C3H/HE (H-$2^k$) marrow (Pierpaoli W. Nat. Immun. 1992; 11:356–365).

Thus if bone marrow or plasma-derived transferrins (Tf) profoundly affect engraftment of allogeneic or xenogeneic bone marrow in lethally irradiated mice and produce a lasting chimerism, it is now considered that the effect observed does not depend on levels or concentrations of Tf and from its saturation with iron, but rather on matching of donor Tf and tissue antigens in the immunosuppressed and transplanted host. The simultaneous presentation of Tf and antigens from a genetically specific donor (mouse, rat, human) in the course of immunoreconstitution results in fact in a state of donor-specific unresponsiveness or tolerance as shown by the acquired inability to mount an immune reaction against the same antigen—and Tf donor and, after bone marrow transplantation, to initiate a graft-versus-host reaction. Applicant thus presently considers that Tf possesses the unique ability to specifically induce specific allo- and xeno-tolerance by a mechanism presently under investigation. It would thus seem that Tf is a major element of the self-recognition and immune mechanisms and that it participates to the development and maintenance of self-tolerance during ontogeny and adulthood.

And indeed, the genetic polymorphism and heterogeneity of human serum transferrin can possibly be considered as directly mimicking the "immune personality" of a human individual: see the article titled "The Biology of transferrin" of de Jong G., Dijk J. P. and Van Ejk, H. C. Clinica Chimica ACTA, 1990, 1–46, Vol. 190.

This makes the invention all the more remarkable as apparently the desensitization of the immune specificity of the transferrins for use in the induction of immune tolerance in a recipient host with respect to antigens, e.g. organs or bone marrow of allogeneic or xenogeneic nature, can be achieved in far easier a manner as it could have seemed. Particularly, it has been found that transferrins, particularly human transferring, obtained from plasma mixtures resulting from the pooling of plasmas obtained from fairly limited numbers of individuals contained all that what is needed to ensure the required tolerance, in most, let alone all humans.

SUMMARY OF THE INVENTION

In accordance with the invention, the transferrins used for the purpose of the invention, consist of a mixture or "pool" of transferrins (hereafter referred to as "pooled transferring" or p-Tf) obtained from a number of donors, sufficient to allow said mixture to contain enough of a variety of transferrins that will allow the pool to contain all the phenotypic information required to ensure for an induction of tolerance against antigens in an immuno-depressed host grafted with said antigens, after that host had been administered an amount of such pooled transferrins effective to induce said tolerance.

In accordance with a preferred embodiment thereof, the invention comprises a biologically active composition effective to control the immune reaction of a host against a donor's antigenic cells or tissue characterized by an active principle consisting of pooled transferrins obtained from a number of donors sufficient to allow said pooled transferrins to contain all the phenotypic information required to ensure for a non-specific induction of immune specific tolerance against antigens of a determined allogeneic donor in an immuno-depressed host grafted with said antigens, after that host had been administered an amount of such pooled transferrins effective to induce said immune specific tolerance.

By "non-specific induction" is meant the capability of the same pooled transferrins to induce said immune specific tolerance in different hosts, as of these pooled transferrins would happen to contain the transferrins of the donor of said antigen or of a phenotypically similar donor, as regard its own transferring.

As will be seen hereafter the immuno-depression can be achieved by an administration to the host of an immuno-suppressive drug, e.g. cyclosporin, prednisolone, cyclosphosphamide, etc . . . or by irradiation.

DESCRIPTION OF THE PREFERRED EMBODIMENTS

Figure 1:
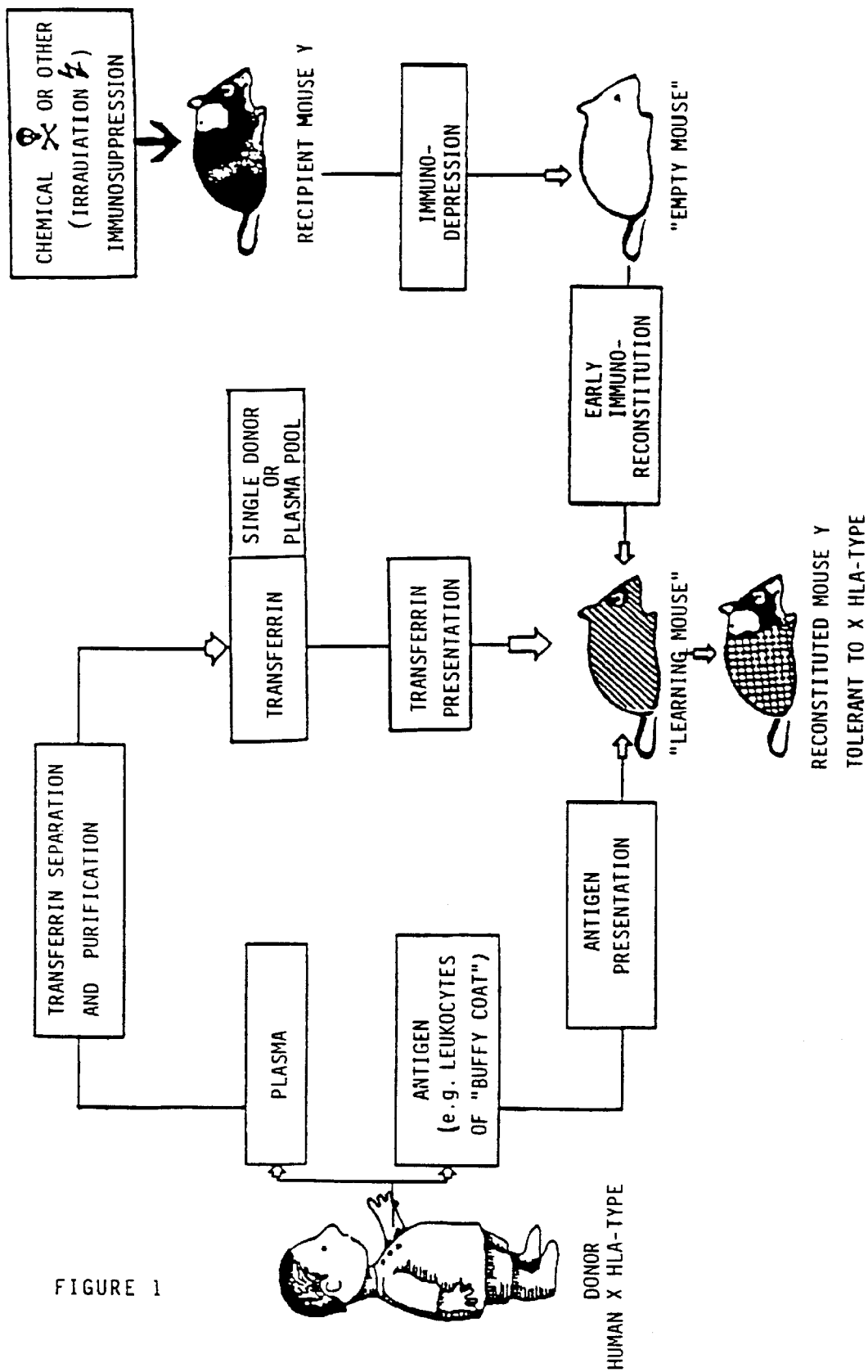
FIG. 1 is an illustration of Applicant's "human to mice model" for the induction of specific transplantation tolerance. In the "human to mice model" immunological tolerance to individual human antigens is induced in chemically immunosuppressed mice with transferrins (either individual or pooled ones) and individual donor leukocytes.

It has been found that complete destruction of the natural immune-system of the host, for instance in leukemia-affected patients undergoing bone marrow transplantation may not be necessary to cure leukemia. The use of chemical immunosuppressants, in conjunction with the pooled transferring, in the appropriate sequences of administration as discussed hereafter may thus be preferable to lethal irradiation. In cancer patients already undergoing an immunosuppressive chemotherapy, the bone marrow (allogeneic or better xenogeneic) grafting, where hold appropriate, may even no longer require a particular administration of an immunosuppressant, in conjunction with both the administration of the pooled transferrins and the grafting operation of said antigens or tissues. Partial or full bone-marrow irradiation as preferably proposed in the grafting protocols proposed by the Applicant in its earlier publications or patents may no longer required.

Advantageously, pooled transferrins are obtained from human plasma pools produced in the industry of blood products. Such plasma pools often originate from several hundreds to several thousands of donors. Advantageously, the transferrins for use in this invention result from the purification product obtained from blood of at least 1000 donors. Thus transferrin pools are readily accessible. And indeed nowadays pooled transferring consist of hemoderivatives deemed as having no therapeutical or clinical uses. They are merely discarded.

The above Clinica Chimica Acta publication should also be used as a reference for the definition of transferring. This expression is to be interpreted broadly. Transferrins are deemed to consist of all molecules which, as indeed provided by that article, are included in that class of counpounds designated as a whole as transferring. They include the so-called apo-transferrins, saturated transferrins, ferro-transferring, etc . . .

Though no relationship has so, far really been established between the genetic diversity of transferrins and the major histocompatibility system in man, the serological detection of a sufficient number of the dominant HLA antigens provides nonetheless an adequate verification system of whether the plasma pools from which the corresponding pooled transferring are to be obtained originated from a sufficient number of donors. For instance a starting plasma pool should prove to contain at least 4 serologically determinable antigens of each of the so-called HLA-A, HLA-B, HLA-C, HLA-D and HLA-DR series. Reference is for instance made to FIG. 3.1, page 70 of the book titled "Medical Immunology" edited in 1979 by James Irvine, Teviot Scientific Publications, Ediburgh, Great Britain.

The invention also concerns the combination of the pooled transferrins as mentioned above and of at least one immunosuppressive drug, e.g. prednisolone, cyclophosphamide, cyclosporin, FK-506 or methatrexate, particularly for use in a human host under the appropriate sequence of administrations, to induce immune tolerance in the host against allogeneic antigens to be grafted in said host.

In the case of organe transplantation, the initial donor's antigens may consist of the "buffy coat" or leucocytes from the donor's peripheral blood after centrifugation, containing granulocytes and lymphocytes with HLA-specific antigenic markers of the individual donor. Most preferably the presentation, e.g. injection of the antigens is done after chemical immunosuppression at the bottom line of endogenous suppression of bone marrow and immune cells and lymphocytes and before the endogenous reconstitution starts. The stage of immuno-suppression can be evaluated in man or animals by leucocyte counts in the peripheral blood. Apparently best results are obtained when the transferrin administration and antigen presentation take place just at the beginning of the endogenous reconstitution, which follows the chemical immunosuppression. The early presentation of antigen buffy coat [e.g. at day 3 in the mouse model of FIG. 1 reported hereafter] together with Tf donor-type or pool, will produce tolerance in said human-to-mouse model. Therefore important elements of this invention comprise the use of pooled transferrins obtained from corresponding plasma pools and the timely injection of the donor antigens, which will induce possibly a selection or deletion of reactive cells [apparently proliferation of specific suppressor cells in the thymus] and thus specific donor-tolerance.

The same considerations do of course apply to other kinds of antigens. Needless to say that the sequence of administration will have to be studied in each case. The antigen to be grafted should not be administered too late after the immunosuppression, particularly when antigen reactive cells will already have been produced again by the recipient host organism. In such event, the recipient host organism will may no longer become tolerant, but be immunized against the antigen.

The invention is not limited to human pooled transferrins, particularly for the above-mentioned uses. It also extends to pooled transferrins of animal origin, particularly for use in conjunction with the grafting even in man of xenogeneic antigens or tissues obtained from the same animal species as the pooled transferrins.

Extraction procedures of transferrins are well known. Some of them are recalled in Applicant's earlier patent EP 0426924 or in the Clinica Chimica Acta publication already referred to hereabove.

Human pooled transferrins may for instance be obtained as disclosed hereinafter.

[A] Preparation of Transferrin (Tf) A pool of human plasma, iron saturated with $Fe^{3+}$ according to Bates G. W. et al, J. Biol. Chem. 1973, 248:3228–32), was diluted in phosphate buffer and diafiltered on hollow fiber cut-off 30000 to remove Fe 3+excess, stored one night at 4° C. and filtered on 0,45μm sterile membranes. The purification procedure consists of two chromatographic steps on ion exchangers, by using buffers at suitable ion strength and pH, in order to selectively remove contaminants such as albumin and immunoglobulins and hence to elute Tf with a purity >95%. After diafiltration to re-establish physiological salt conditions, the solution of apo- or saturated Tf was freeze-dried.

[B] Induction of Transplantation Tolerance

The experimental protocols which have been used are briefly recalled hereafter, prior to being set forth subsequently in a more detailed manner.

Prednisolone (Pr) and cyclosphosphamide (Cy) were chosen as immunosuppressants; their respective dosages were adjusted in different mouse strains according to changes in their immunological parameters. By using this model, the first indications of the tolerence-inducing activity of Tf were observed in preliminary studies on the immune response to human erythrocytes. It was found that Tf treatment in immunosuppressed and antigen treated inhibits the primary and the secondary immune response to human red blood cells (HRBC) (Table 1).

Since histocompatibility antigens are presented mostly on leukocytes, but not on erythrocytes, it was important to know whether Tf treatment can induce donor-specific transplantation tolerance in mice immunized with peripheral blood "buffy coat" leukocytes. In fact, the abrogation of cell-mediated immune response towards the Tf donor tissue antigens was demonstrated with the popliteal lymph node assay in chemically immunosupressed mice treated with Tf of the donor (Table II).

Figure 2:
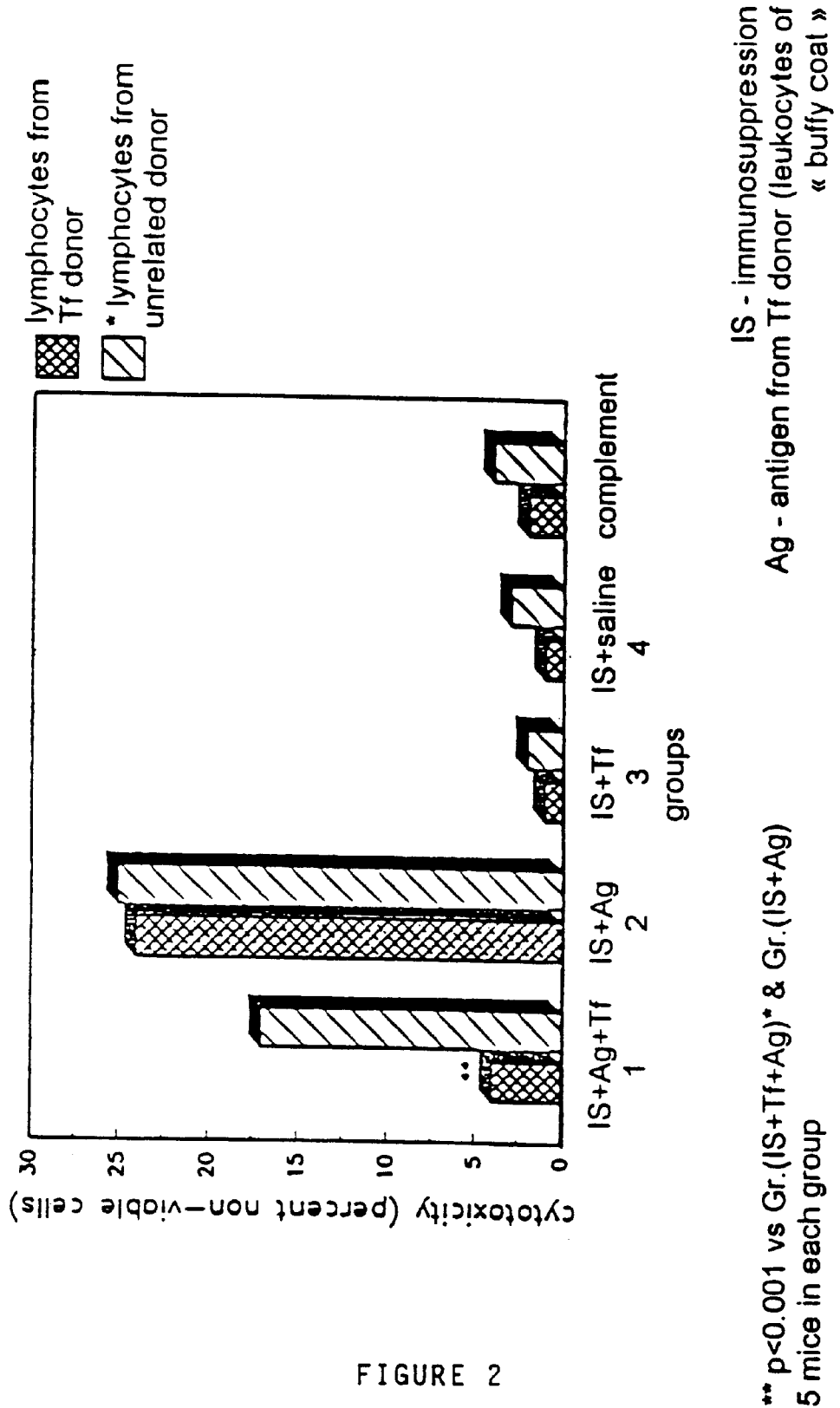
FIG. 2 provides for the graphical evidence of tolerance, by the establishment of the absence of specific antibody and complement mediated cytotoxicity of "tolerant" mouse serum towards human lymphocytes from transferrin (Tf) donor: Trypan-blue exclusion assay.

Also absence of donor-specific antibody- and complement-mediated cytotoxicity of mouse serum towards human lymphocytes in chemically immunosuppressed mice treated with human individual Tf or p-Tf was confirmed by trypan-blue exclusion assay (FIG. 2 and Table III).

From the data presented here, it is possible to see that also the administration of Tf from a human plasma pool, combined with critically timed presentation of individual specific tissue antigens can produce a state of immunological tolerance. Besides tolerance-inducing properties, human pooled transferring also possess a remarkable immunoprotective activity by preventing thymus involution and lymphopenia and by increasing the survival rate of chemically immunosuppressed mice.

The above mentioned human-to-mouse model and the results point to a clear-cut tolerance-inducing effect of human transferrin by combined administrations of pooled Tf and cell antigens. Individual Tf alone is not immunosuppressive and is unable to produce tolerance to human antigens in the mouse.

The implication deriving from the disclosed models are obvious. Such transplantation system should be adaptable to larger mammals and to man. In addition, the understanding of the mechanism by which p-Tf from plasma pools produces tolerance certainly deserves intensive investigations for a possible adaptation of the model to a number of pathological conditions such as cancer, autoimmune disease, immunodeficiency diseases (AIDS), genetic defects or diabetis.

The description will further be amplified hereafter without any limitative intent, e.g. with reference to the drawings in which 1) The Comparative Effects of INDIVIDUALS• Tf and of Pooled Tf on the Primary and the Secondary Immune Responses to Human Red Blood Cells (HRBC)• in Chemically Immunosuppressed Mice (Results from ight similar experiments).

Both the individual Tf and the HRBC originated from the same human donors. The hemagglutination test that has been used is described hereafter.

The principle is that specific bivalent antibodies bind to antigens present on the test red cells, causing them to agglutinate.

The primary immune response (IR) to human red blood cells (HBRC) was determined 7 days after the first immunization with 0,2 ml 10% red cell suspension or 0,2 ml whole blood from Tfs donor intraperitoneally; the secondary IR was determined 5 days after the second immunization with the same antigen.

The mouse blood was collected separately from each mouse by using a single punching of the mandibular vein or after decapitation. The blood serum was separated by centrifugation (1500 rpm, 10 min) and stored at –70° C. until the assay. At the test day the mouse serum was inactivated by heating in water bath (56° C., 30 min). Tissue culture 96-wells plate with V-shape bottom were used for determination of the serum antibody titer towards HRBC used for immunization of the mice. Serum dilution.

Saline was distributed into wells of the plate (50 μl into each well). For each sample 50 μl the serum under study was added into the first well and mixed. 50 μl of this mixture was passed into the second well, mixed and passed to the next wells by an identical way. So, the serum of each sample was diluted by 2, 4, 8, 16, . . . 4096 times. The serum dilutions were expressed in - log2 antibody titer (1, 2, 3, 4, . . . 12).

After adding 50 μl of 2% HRBC suspension into each well the mixture was incubated in thermostat (37° C., 1 hour); after that the plate was ready to be read. For each individual serum the result was determined as the last maximal dilution of the serum where HBRC agglutination was observed.

The results of this agglutination test as applied to the above-mentioned comparative data do establish that the pooled transferrins exerted substantially the same effect as the individual ones. The results are presented in Table I.

TABLE I

The effect of Tf (individual° or pool) on the primary and secondary immune response to human red blood cells (HRBC)° in chemically immunosuppressed mice.
(Results from eight similar experiments)

| | (-log 2 titers of antibody) | |
|---|---|---|
| Gr. No | primary response | secondary response |
| 1. normal immunized control | 6.4 ± 0.3 (n = 31) | 8.2 ± 0.5 (n = 24) |
| 2. IS + HSA | 4.5 ± 0.7 (n = 31) | 7.4 ± 0.5 (n = 24) |
| 3. IS + Tf bovine | 2.7 ± 0.8 (n = 11) | 7.7 ± 0.7 (n = 10) |
| 4. IS + Tf human (pool) <<Sigma)>> | 1.8 ± 0.5** (n = 24) | 4.3 ± 0.7* (n = 24) |

TABLE I-continued

The effect of Tf (individual° or pool) on the primary
and secondary immune response to human red
blood cells (HRBC)° in chemically
immunosuppressed mice.
(Results from eight similar experiments)

| | (-log 2 titers of antibody) | |
|---|---|---|
| Gr. No | primary response | secondary response |
| 5. IS + Tf human from individual plasma° | 1.7 ± 0.5** (n = 28) | 5.3 ± 0.8** (n = 42) |

*p < 0.001 vs Gr. 1,2; **p < 0.02 vs Cr 1,2
IS - immunosuppression, Tf - transferrin;
n - number of mice per group, HSA - human serum albumin
°individual Tf and HRBC were obtained from the same person 2) The Effect of Tf (Individual or Pooled) on the Delayed Type Hypersensitivity Response in Chemically Immunosuppressed Mice (Popliteal Lymphnode Assay)

Generally speaking the delayed type hypersensitivity response (specific) by popliteal lymph node test (PLNT) was assessed as follows.

The PLNT is performed on mice previously immunized with tissue antigens of Tf donor. At the test day all mice are injected into the right hind foot pad with $5 \times 10^5$ buffy coat leucocytes from a Tf donor in 25 μl and the same number of leukocytes from an unrelated donor into the left hind foot pad. The mice were sacrificed eight days later. The popliteal lymph nodes were isolated and their wet weight was recorded. Lack of increase of the right lymph node in mice treated with transferrin expresses the abrogation of cell-mediated immune response towards Tf donor tissue antigens used for immunization.

More specifically the test was run as follows.

Mice were chemically immunosuppressed by i.p. injection of 100 mg/kg prednisolone (Pr) and 50 mg/kg cyclophosphamide (Cy) on day 0. On day 1, 100 mg/kg Cy were injected again i.p. Three weeks after the treatment, the mice were treated again according to the same schedule with 75 mg/kg Pr and 50 mg/kg Cy and again with 100 mg/kg of Cy. Four weeks after the second immunosuppressive treatment, the mice were injected with the same amounts of Pr an Cy as the second round. After each immunossuppressive treatment, the mice of groups 1 and 2 were treated from day 3 to day 5 i.p. with a daily injection of donor-specific V.L. or pool Tf[1], 200 μg/0,5 ml into each mouse. Control group 3 was injected with the same amount of human serum albumin (HSA). Group 4 (only immunosuppressed) was left untreated similarly to group 5 (intact mice). At 66 and 73 days after initiation of the experiment, all mice were immunized twice i.p. with V.L. antigens, namely $o,5 \times 10^6$ V.L. peripheral blood buffy coat leukocytes in 0,3 ml and 0,2 ml V.L. 10% erythrocyte suspension in saline. The mice were treated again with Tf or HSA (or left untreated, groups 4 and 5) for three days after immunization, at the daily dose indicated above, i.p. The popliteal lymphnode test (PLNT) was performed at day 95 after initiation, by injecting all mice into the right hind foot pad with $5 \times 10^5$ V.L. buffy coat leukocytes in 25 μl and the same number of leukocytes from an unrelated donor into the left hind foot pad. The mice were sacrificed eight days later and the weights of the popliteal lymphnodes were recorded. Lack of increase of the right lymphnode in group 1 (Tf V.L.) and in group 2 (Tf pool) express the abrogation of cell-mediated immune response towards V.L. tissue antigens (transplantation tolerance). It can be noted that also Tf pool decreases the reaction to third party antigen (group 2, left popliteal lymphnode).

The results are presented in table II.

TABLE II

Induction of donor-specific transplantation tolerance
in chemically immunosuppressed (IS) and transferrin (Tf) - treated mice
(popliteal lymph mode test - PLNT)

| Groups | Left PLN (mg) Ag unrelated donor | Right PLN (mg) Ag V.L. | L-R |
|---|---|---|---|
| 1. IS + Tf V.L. n = 5 | 2.64 ± 0.38 | 1.08 ± 0.14 | 1.56 ± 0.40* |
| 2. IS + Tf pool n = 5 | 1.48 ± 0.19 | 1.08 ± 0.12 | 0.40 ± 0.10** |
| 3. IS + HSApool n = 5 | 2.54 ± 0.33 | 2.18 ± 0.42 | 0.36 ± 0.34 |
| 4. IS + untreated n = 5 | 1.60 ± 0 | 2.20 ± 0.20 | -0.60 ± 0.20 |
| 5. intact n = 5 | 0.92 ± 0.10 | 0.95 ± 0.10 | -0.03 ± 0.09 |

*p < 0.02 vs Gr. 2, 4; p < 0.05 vs Gr. 3.
**p < 0.01 vs Gr. 4.

ANTIBODY AND COMPLEMENT-MEDIATED CYTOTOXIXITY TEST FOR TOLERANCE

Trypan-blue Exclusion Assay

The assay consists of testing the permeability of cells after their incubation with antibody and complement. If cytotoxic antibodies bind to the membranes of target cells, complement is fixed and cell permeability increases. It is used to assess cell permeability or "death" by adding a solution of trypan blue which penetrates into dead cells, but leaves viable cells unstained.

Donor human lymphocytes were isolated by using histopaque 1070 (Sigma, U.S.A.) and resuspended in concentration $6-8 \times 10$/ml.

Balb/C mice were chemically immunosuppressed by i.p. 90mg/kg prednisolone (Pr) and 100 mg/kg cyclophosphamide (Cy) on day 0. On day 1, 100 mg/kg Cy were injected again i.p. with a daily injection of W. P. Tf (group 1) or Tf from human plasma pool (group 2), 200 μl/0,5 ml into each mouse. W. P. are the initials of the name and first name of the persons from whom the antigens and/or individual donor specific Tf are derived.

The mice of all groups were immunized twice i.p. with W. P. antigens (Ag), namely $1,5 \times 10$ W. P. peripheral blood "buffy coat" leukocytes in 0,3 ml on day 3 and day 16. The mice were sacrificed on day 31 of the experiment, the serum of all mice was collected and the trypan-blue exclusion assay was performed.

At the day of assay the serum from each mouse was complement-inactivated by heating to 56° C. for 30 min. Samples of mouse serum were dispensed in 25 μl volume. An equal volume of human lymphocytes suspension was added to each tube and the mixture was incubated at 37° C. for 30 min. Then 50 μl rabbit complement (Sigma, USA) was added to each sample, and incubation was carried out for 10 min at 37° C. Controls were set up using normal mouse serum or saline to ensure that the complement is non-toxic.

After centrifugation (2000 rpm, 5 min) the supernatant fluid was removed from each tube leaving the cells undisturbed at the bottom and tubes are immersed into the ice. 25 μl trypan blue solution (Sigma, USA) was added to each tube and the proportion of stained cells counted using light microscopy (Zeiss, Germany) and Gorjaev's chamber (modified Neubauer chamber).

The results are provided in Table III hereafter. They are also presented graphically in FIG. 2.

TABLE III

Complement-mediated cytoxicity of mouse serum towards human lymphocytes in chemically immunosuppressed (IS) mice treated with human individual or pool transferrin (Tf) (Trypan-blue exclusion assay)

| | % of dead cells | |
|---|---|---|
| Groups | Lymphocytes of Tf donor (W.P.) | Lymphocytes of unrelated donor |
| 1. IS + Ag W.P. + Tf W.P. ᵇ | 5.3 ± 1.1* | 14.1 ± 1.3° |
| 2. IS + Ag W.P. + Tf pool ᵇ | 6.4 ± 1.6* | 3.8 ± 0.5°° |
| 3. IS + Ag W.P. | 26.2 ± 7.6 | 20.6 ± 4.2 |
| 4. non - IS + Ag W.P. | 91.0 ± 5.1 | 86.6 ± 8.3 |
| complement-control | 0.9 | 0.9 |

* -p < 0.05 vs Gr.3; °p < 0.001 vs Gr. 1 (Lymph. of Tf donor); °°p < 0.01 vs Gr.3 n = 5 in each group 4) Model for Bone Marrow Transplantation (BMT)

Engraftment of rat bone marrow (BM) and donor-specific (rat) hemopoietic chimerism are achieved in lethally irradiated mice by the combined administration of donor-derived (rat) BM and transferrin (Tf).

Balb/c mice were irradiated 850 rad TBI; C57Bl/6 mice 950 rad. About 24 hours after TBI (day 1) and one hour before BM injection, the mice were injected i.v. or i.p. with 100 to 200 μg of albumin (controls) or ironsaturated human or rat transferrin. They were injected again with the same dose on day 2 and 3 after TBI, i.p. All the mice were inoculated one hour after the initial transferrin treatment with 12 to 15 millions of rat BM cells derived of the original suspension medium and resuspended in 0,5 ml, 25 hours after TBI.

Permanent and complete chimerism was assessed in all surviving mice by the presence of alkaline phosphatase-positive (rat) granulocytes in peripheral blood, complete unresponsiveness (no antibody formation) to donor rat erythrocytes (primary and memory response) and, in selected groups, inability to reject xenogeneic skin grafts from the BM (rat) donors (FIG. 1).

-iron-saturated, Sigma, St Louis, USA.
-iron-saturated, from plasma of BM rat donors (inbred) Rii/2., Sclavo Inc. Siena, Italy; HSA: Human serum albumin, SA: rat serum albumin.

The results are presented in Table IV.

TABLE IV

MODEL FOR BONE MARROW TRANSPLANTATION (BMT) Engraftment of rat bone marrow (BM) and donor-specific (RAT) hemopoietic chimerism are achieved in lethally irradiated mice by the combined administration of donor-derived (RAT) BM and transferrin (Tf)

| Groups Treatment | Recipeint strain | Mouse (number) | Percent of surviving chimeric mice after BMT (months) | | | | | |
|---|---|---|---|---|---|---|---|---|
| | | | 2 | 4 | 6 | 8 | 10 | 12 |
| A Human Albumin | Balb/C | (25) | 28 | 8 | 4 | 0 | | |
| B Human Tf a | Balb/C | (25) | 32 | 8 | 0 | | | |
| C Rat Tf a | Balb/C | (20) | 60 | 40 | 20 | 10 | 0 | |
| D Rat Albumin | Balb/C | (50) | 46 | 20 | 0 | | | |
| E Tf from BM donor b | Balb/C | (30) | 86 | 73 | 63 | 57 | 53 | 43 |
| F Rat Albumin | C57Bl/6 | (30) | 60 | 40 | 3 | 0 | | |
| G Tf from BM donor b | C57B16 | (30) | 93 | 83 | 70 | 67 | 69 | 53 | a) Tf from plasma pool (Sigma)
b) Rat Tf from plasma of BM donor (SCLAVO)

The compositions of the invention are suitable for use in the many areas, some of which have already been referred to earlier. These compositions are suitable particularly for the treatment of the following classes of diseases, all of which would benefit of bone marrow in vivo transplantation:

Aplastic anemia agranulocystosis;
Thalassemia;
Immunodeficiency diseases (AIDS, agammaglobulinemia, etc.);
Leukemias (Myeloblastic, lymphoblastic, erythtroblastic, etc.) Myelomas;
Solid tumors, carcinomas, adenocarcinomas;
Genetic diseases
Organ transplantation. Another large group of therapies can make use of the invention, e.g.: from man or animals (pig, monkey, etc.) (Acceptance of liver, heart, kidneys without rejection reaction). Langerhans islets for the treatment of diabetis.

Whenever required the patient may be preconditioned to the immune acceptance of an organ or tissue from another host, by prior transplantation of bone marrow from the host which is also to provide said organ or tissue.

See also general indications supplied by Gluckman E. in its article titled "Bilan actuel de la greffe de moelle osseuse allogenique" (General overview on the graft of allogeneic bone marrow) published in Path. Biol. 1980, 28, N° 1, 5–7. These indications are also applicable here.

The invention finds use preferably in the graft of allogeneic (histoincompatible non-HLA-matched) BMT, whereby the difficulties linked to the finding of a donor should be circumvented to a great extent. The invention is not limited to compositions for use in the graft of allogeneic BMT only. Their use is to be contemplated in any system aiming at facilitating the engraftment of any type of bone marrow in any type of mammal including man.

Though the way of administering the composition of the invention and its coupling with the steps involving depression or suppression of the endogeneous immunitary system in the host to be transplanted with allogeneic on xenogeneic bone marrow should rest with the clinicians, it nevertheless remains that the abovesaid depression or suppression should normally be caused to take place prior to the transplantation.

Noteworthy is the fact that chemical immunosuppression of the receiving host prior to transplanting the bone marrow or other antigen or tissue to be grafted should generally be enough. What is required in most instances is the induction of a tolerance to the allogeneic, or even xenogeneic antigens. Full previous destruction of the receiving host's own immune system does not appear as necessary. But the systems used to induce immunosuppression in the host may also combine chemical immunosuppression with more or less limited irradiation, for instance of lymphoid organs only, in order to prevent large irradiation damage (lungs, intestine, etc.). Any cytostatic drug or immunosuppressive drug, e.g. cyclosporin, prednisolone, FK-506 may be given alone or in combination with irradiation to condition the recipient to the transfer of bone marrow.

Neither are the uses of the compositions of the invention limited to the transplantation of bone marrow only. They become applicable whenever a transfer into the treated host of a new immunological system is required, e.g. for inducing rejection by the host of leukemia cells, solid tumors. Another important use of the invention is in xenogeneic (interspecies) BMT, for example when the donor of bone marrow and organs (liver, heart, kidneys) is the pig or a primate (monkeys) and the receiver is man.

Alternatives in the moments at which the transferrin pools are to be administered are contemplated too. They may also be administered to the donor, prior to the transfer of its bone marrow to the recipient. But repeated subsequent administrations of said transferrin pools is likely to favor the engraftment-capacity of the bone marrow or others organs or tissue in the recipient, in order to reinforce the tolerance induced towards the grafted bone marrow and organs or tissue of allogeneic or xenogeneic origin.

Pooled transferrins may also be added to bone marrow cultures, to pre-incubate in vitro the donor bone marrow for variable periods (hours or days) before its inoculation in the recipient. This procedure may change and/or improve the engraftment capacity of the donor bone marrow and enhance induction of GvHd-free chimerism.

The compositions of the invention may be administered by any route normally used to enhance the host non-responsiveness to the foreign (allogeneic or xenogeneic) bone marrow and/or organs. Though oral or rectal routes may be contemplated, the preferred ones remain the parenteral routes (intravenous or intramuscular injections).

Though this should not be construed in any limitative manner whatsoever, daily doses of pooled transferrins to the host after the engraftment of bone marrow and/or organs sought to be grafted has been achieved, should normally range from about $5 \times 10^6$ MM per kg body weight of the host. Treatments of that type should normally last from 10 to 30 days after said engraftment.

However, the treatment with the pooled transferrins may also be pursued days, weeks or months after transplantation of bone marrow alone or in combination with immunosuppresive drugs such as e.g. cyclophosphamide, cyclosporin, FK-506, methotrexate in all those cases in which the transplanted individual shows signs or symptoms of an ill-functioning hemopoietic system (anemia, leucopemia, trombocytopemia or of graft versus host disease) and/or immunological deficiencies (parasitic, viral or bacterial infections).

It should finally be emphasized that the invention is not limited to the use, for the production of the abovesaid pharmaceutical compositions, of the natural pooled transferrins of natural origin, essentially as contemplated hereabove.

The active principles of these compositions may also consist of mixtures of sufficient a mixture of genetically engineered transferring, e.g. of the expression products in appropriate host cells of a mixture of the cDNAs (or of fragments of said cDNAs) obtained from corresponding mixtures of RNAs themselves obtained, e.g. from natural the lymphocytes obtained from natural plasma pools.

What is claimed is:

1. A method for controlling immune reactions to a foreign tissue or a foreign cell in a recipient host mammal to enhance a tolerance of said recipient host mammal towards a grafted foreign tissue or a grafted foreign cell, said method comprising the step of:

(a) administering a transferrin from a genetic donor and a foreign tissue or a foreign cell antigen from the same genetic donor as the transferrin to said recipient host mammal wherein said recipient host mammal is immunosuppressed prior to administering said transferrin for a time and under conditions effective to control immune reactions by enhancing tolerance.

2. The method according to claim 1, wherein said transferrin and said foreign tissue or said foreign cell antigen are administered simultaneously.

3. The method according to claim 1, wherein said recipient host mammal is immunosuppressed with an immunosuppressive drug.

4. The method according to claim 3, wherein said immunosuppressive drug is selected from the group consisting of prednisolone, cyclophosphamide, cyclosporin, methotrexate and FK-506.

5. The method according to claim 1, wherein said grafted foreign cell is a bone marrow cell.

6. The method according to claim 5, wherein said bone marrow cell is allogeneic in origin.

7. The method according to claim 5, wherein said bone marrow cell is xenogeneic in origin.

8. The method according to claim 1, wherein said transferrin is a pooled transferrin.

9. The method according to claim 8, wherein said pooled transferrin is obtained from pooled blood of donors which comprises at least four serologically determinable antigens of each of the HLA-A, HLA-B, HLA-C, HLA-D and HLA-Dr series.

10. The method according to claim 8, wherein said pooled transferrin is a human pooled transferrin.

11. A method for controlling immune reactions to a foreign tissue or a foreign cell in a recipient host mammal to enhance a tolerance of said recipient host mammal towards a grafted foreign tissue or a grafted foreign cell, said method comprising the step of:

(a) administering a pooled tansferrin from a specific species and a foreign tissue or a foreign cell antigen from the same specific species as the pooled transferrin to said recipient host mammal wherein said recipient host mammal is immunosuppressed prior to administering said pooled transferrin for a time and under conditions effective to control immune reactions by enhancing tolerance.

12. A method for grafting a donor foreign mammalian tissue or foreign mammalian cells into a recipient host mammal, said method comprising the steps of (a) immunosuppressing the recipient host mammal;

(b) grafting the immunosuppressed host with said foreign mammalian tissue or foreign mammalian cells; and (c) combining said grafting with the administration of a transferrin for inducing specific immune tolerance in the recipient host mammal against said foreign mammalian tissue or foreign mammalian cells
wherein said transferrin is from a genetic donor and said foreign mammalian tissue or said foreign mammalian cells are from the same genetic donor as the transferrin for a time and under conditions effective to control immune reactions by enhancing tolerance.

13. The method according to claim 12, which further comprises causing said foreign mammalian tissue or said foreign mammalian cells and said transferrin to be present simultaneously in the recipient host mammal in the course of the immunoreconstitution in said recipient host mammal.

14. A method for grafting a donor foreign mammalian tissue or foreign mammalian cells into a recipient host mammal, said method comprising the steps of (a) immunosuppressing the recipient host mammal;

(b) grafting the immunosuppressed host with said foreign mammalian tissue or foreign mammalian cells; and (c) combining said grafting with the administration of transferrin for Inducing specific immune tolerance in the recipient host mammal against said foreign mammalian tissue or said foreign mammalian cells wherein said transferrin is a pooled transferrin from a specific species and said foreign mammalian tissue or foreign mammalian cells are from the same specific species as the pooled transferrin for a time and under conditions effective to control immune reactions by enhancing tolerance.

15. The method of claim 14, which further comprises causing said foreign mammalian tissue or said foreign mammalian cells and said pooled transferrin to be present simultaneously in the recipient host mammal in the course of the immunoreconstitution in said recipient host mammal.

16. The method of claim 14, wherein said pooled transferrin is obtained from pooled blood of donors which comprises at least four serologically determinable antigens of each of the HLA-A, HLA-B, HLA-C, HLA-D and HLA-Dr series.

17. The method of claim 14, wherein said pooled transferrin consists of a mixture of transferrins obtained from a sufficient number of individuals to reduce a state of donor-specific immunoresponsiveness or tolerance against the foreign mammalian tissue or foreign mammalian cells in said recipient host mammal.

18. A method for controlling immune reactions to a xenogeneic foreign tissue or a xenogeneic foreign cell in a recipient host mammal to enhance a tolerance of said recipient host mammal towards a grafted foreign tissue or a grafted foreign cell, said method comprising the step of:

(a) administering a pooled transferrin which matches a donor transferrin and a xenogeneic foreign tissue or a xenogeneic foreign cell antigen to said recipient host mammal wherein said recipient host mammal is immunosuppressed prior to administering said pooled transferrin for a time and under conditions effective to control immune reactions by enhancing tolerance.

* * * * *